United States Patent [19]

Rauleder et al.

[11] 4,436,943
[45] Mar. 13, 1984

[54] PROCESS FOR THE PREPARATION OF 2,2-DICYCLOHEXENYLPROPANE

[75] Inventors: Gebhard Rauleder, Haan; Helmut Waldmann, Leverkusen, both of Fed. Rep. of Germany

[73] Assignee: Bayer Aktiengesellschaft, Leverkusen, Fed. Rep. of Germany

[21] Appl. No.: 477,464

[22] Filed: Mar. 21, 1983

[30] Foreign Application Priority Data

Mar. 26, 1982 [DE] Fed. Rep. of Germany ....... 3211304

[51] Int. Cl.$^3$ .............................................. C07C 1/20
[52] U.S. Cl. ..................................... 585/357; 585/360
[58] Field of Search ................................. 585/357, 360

[56] References Cited

U.S. PATENT DOCUMENTS 3,085,121  4/1963  Guest et al. .......................... 585/357
3,167,595  1/1965  Heywood et al. ................... 585/357

*Primary Examiner*—Curtis R. Davis
*Attorney, Agent, or Firm*—Sprung, Horn, Kramer & Woods

[57] ABSTRACT

2,2-Dicyclohexenylpropane is prepared by heating 4,4'-dioxydicyclohexylpropane in the presence of a strong acid, under pressures from 1 to 50 mbar and at 120° to 220° C., distilling off the 2,2-dicyclohexenylpropane produced with the water formed and separating the water out of the top product from the distillation.

9 Claims, No Drawings

PROCESS FOR THE PREPARATION OF 2,2-DICYCLOHEXENYLPROPANE

The present invention relates to a process for the preparation of 2,2-dicyclohexenylpropane by dehydration of perhydrogenated 4,4'-dioxydiphenylpropane (in the following text, 4,4'-dioxydiphenylpropane is also designated bisphenol A, and perhydrogenated 4,4'-dioxydiphenylpropane is also designated 4,4'-dioxydicyclohexylpropane).

2,2'-Dicyclohexenylpropane is a known chemical compound which finds use in the preparation of polymers, as an organic intermediate and for the preparation of 2,2-dicyclohexenylpropane diepoxide.

Suggestions have already been made for the preparation of 2,2-dicyclohexenylpropane by splitting off water from perhydrogenated bisphenol A in accordance with the following equation:

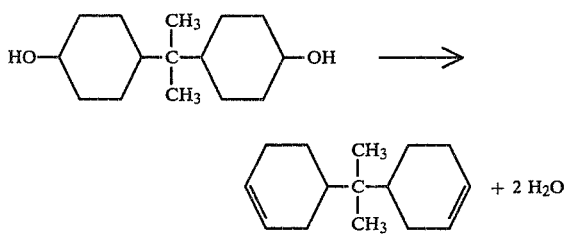

Thus, in Example 1 of German Patent Specification No. 857,961, a process of this type is described in which perhydrogenated bisphenol A is heated with approximately twice the amount by weight of anhydrous potassium bisulphate at 160° C. for 8 hours. Following this, the mixture has to be washed with water and the organic product has to be distilled. No yields are reported. However, this process is little suited for industrial use since, after working up, large amounts of environmentally deleterious aqueous salt solutions result.

Nor does the process described in German Auslegesschrift No. 1,099,733 offer any advantage. In Example (A) in the latter, the preparation of 2,2-dicyclohexenylpropane by dehydration of 340 g of perhydrogenated bisphenol A with 4 g of β-naphthalenesulphonic acid and 900 g of a milled dehydration mixture, which consists of equal parts of potassium bisulphate and dry sand, is described. The water formed during the reaction is continuously distilled off. After the end of the reaction, the product is taken up with ether, washed with water to neutrality, dried with calcium chloride and the ether is distilled off in vacuo. The disadvantages of this process are the same as those mentioned above, and the yield is about 60% of theory.

A process for the preparation of 2,2-dicyclohexenylpropane from 4,4'-dioxydicyclohexylpropane has now been found, which is characterized in that 4,4'-dioxydicyclohexylpropane is heated in the presence of a strong acid under a pressure of 1 to 50 mbar and at temperatures in the range 120° to 220° C., the 2,2-dicyclohexenylpropane produced, together with the water formed, is distilled out of the reaction mixture and the water is separated out of the top product from this distillation.

The starting product for the process according to the invention, perhydrogenated 4,4'-dioxydiphenylpropane, can be obtained, for example, by hydrogenation of 4,4'-dioxydiphenylpropane (bisphenol A) (see German Auslegeschrift No. 1,099,733).

Strong acids suitable for the process according to the invention are all strong acids which are stable under the reaction conditions. Strong acids of low volatility are preferably employed, for example arylsulphonic acids or mineral acids, such as sulphuric acid or phosphoric acid. p-Toluenesulphonic acid is preferably employed.

The concentration of the acid in the reaction mixture can vary within wide limits. For example, concentrations from 0.5 to 10% by weight are suitable. Concentrations of 0.75 to 5% by weight are preferred and those from 1 to 2% by weight are particularly preferred.

The process according to the invention can generally be carried out such that perhydrogenated bisphenol A and the strong acid are mixed, a pressure in the range from 1 to 50 mbar is set up, the temperature is raised to the range from 120° to 220° C. and the 2,2-dicyclohexenylpropane produced, together with the water produced, is distilled off. The pressure and the temperature can also be adjusted in the reverse sequence or simultaneously. In any case, the pressure and temperature should be combined within the ranges indicated so that 2,2-dicyclohexenylpropane and water distil off. Temperatures from 160° to 210° C. and pressures from 5 to 50 mbar are preferably used, and temperatures from 185° to 200° C. and pressures from 10 to 20 mbar are particularly preferably used.

Apart from the procedure under isothermal conditions, that is to say maintenance of a uniform temperature during the reaction, the reaction can also be carried out with the setting up of a so-called temperature gradient, that is to say at temperatures varying within the limits indicated.

The 2,2-dicyclohexenylpropane distilling off and the water distilling off can be condensed together or separately. In the case of joint condensation, two phases form and, after separating off the aqueous phase, 2,2-dicyclohexenylpropane remains. In the case of separate condensation, initially only 2,2-dicyclohexenylpropane condenses at a higher temperature and subsequently the water at a lower temperature. If volatile strong acids have been employed, after the reaction these are generally found in the aqueous phase and can be removed together with the latter. When the preferred strong acids of low volatility are employed, these remain in the bottoms of the distillation and can be used again for new batches.

In a preferred industrial embodiment of the process according to the invention, perhydrogenated bisphenol A is initially introduced with about 1 to 2% by weight of p-toluenesulphonic acid and, under a pressure of 10 to 20 mbar, heated to temperatures of 190° to 200° C. The 2,2-dicyclohexenylpropane formed during the reaction, together with the water formed, is continuously distilled out of the reaction mixture, while fresh perhydrogenated bisphenol A is continuously metered into the reactor. The product resulting during this at the top of the distillation, which essentially consists only of 2,2-dicyclohexenylpropane and water, is cooled down and transferred to a separator, in which two phases form. The aqueous phase is separated off and the remaining organic phase is pure or almost pure 2,2-dicyclohexenylpropane.

In another preferred industrial embodiment, the condensation is carried out such that only the 2,2-dicyclohexenylpropane is condensed in a first condenser, while the water is obtained at a lower temperature in a second condenser.

2,2-Dicyclohexenylpropane can be obtained with the process according to the invention in a yield of more than 95% of theory, having a water content below 0.1% by weight and in a purity of more than 99%. The water of reaction which has been separated off can optionally be freed of small amounts of organic compounds present therein simply by brief stripping.

The advantage of the process according to the invention consists of the economical accessibility of 2,2-dicyclohexenylpropane in a simple manner with high yields and in high purity, and the possibility of avoiding the use of large amounts of salt, which lead to environmentally deleterious effluents.

EXAMPLE 600 g of perhydrogenated bisphenol A and 9 g of p-toluenesulphonic acid were initially introduced into a stirred reactor having a distillation column on top. A pressure of 15 mbar was set up, with stirring, and the mixture was heated to 195° C. The 2,2-dicyclohexenylpropane produced, together with the water of reaction, distilled off. At the start of the distillation, the metering in of fresh perhydrogenated bisphenol A was started up. The pump was adjusted so that a constant level of reaction mixture was set up in the reactor. 175 g of perhydrogenated bisphenol A were metered in each hour. At the top of the column, 2,2-dicyclohexenylpropane was obtained in a first condenser and the water of reaction, which had separated out and which was freed in a separator from small amounts of 2,2-dicyclohexenylpropane which had been carried over, was obtained in a second condenser. The latter was returned to the distillation column.

2,2-Dicyclohexenylpropane was obtained in an amount of 143.8 g each hour, corresponding to a yield of 96.3% of theory. The purity of the 2,2-dicyclohexenylpropane separated off was 99.6%.

What is claimed is:

1. A process for the preparation of 2,2-dicyclohexenylpropane which comprises heating 4,4'-dioxydicyclohexylpropane in the presence of a strong acid, under a pressure of 1 to 50 m.bar and at a temperature in the range of from 120° to 220° C. and distilling off 2,2-dicyclohexenylpropane together with water formed from the reaction mixture and separating water from the top product of the distillation.

2. A process according to claim 1, wherein the strong acid is employed in an amount of 0.5 to 10% by weight based upon the weight of the reaction mixture.

3. A process according to claim 1, wherein said strong acid is p-toluenesulphonic acid, sulphuric acid or phosphoric acid.

4. A process according to claim 1, wherein the process is carried out at a temperature from 160° to 210° C. under a pressure of from 5 to 50 m.bar.

5. A process according to claim 1, wherein 2,2-dicyclohexenylpropane and water formed as a result of the process are distilled altogether and condensed together and the aqueous phase resulting from the condensation is separated from the organic phase.

6. A process according to claim 1, wherein 2,2-dicyclohexenylpropane and water formed during the process are distilled off and condensed separately, the 2,2-dicyclohexenylpropane is separated off in a first condensation zone and the water is separated off in a second condensation zone operated at a temperature lower than the temperature of the first condensation zone.

7. A process according to claim 1, wherein the process is carried out in the absence of potassium bi-sulphate.

8. A process according to claim 1, wherein the strong acid is employed in an amount of 0.75 to 5% by weight based upon the weight of the reaction mixture.

9. A process according to claim 1, wherein the strong acid is employed in an amount of 1 to 2% by weight based upon the weight of the reaction mixture.

* * * * *